(12) United States Patent
Brodbeck

(10) Patent No.: US 8,808,316 B2
(45) Date of Patent: Aug. 19, 2014

(54) DEVICES AND METHODS FOR PRODUCING ANASTOMOSES

(75) Inventor: Achim Brodbeck, Metzingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 146 days.

(21) Appl. No.: 13/383,937

(22) PCT Filed: Jul. 13, 2010

(86) PCT No.: PCT/EP2010/004259
§ 371 (c)(1),
(2), (4) Date: Jan. 13, 2012

(87) PCT Pub. No.: WO2011/006639
PCT Pub. Date: Jan. 20, 2011

(65) Prior Publication Data
US 2012/0116428 A1  May 10, 2012

(30) Foreign Application Priority Data

Jul. 14, 2009 (DE) .......................... 10 2009 032 972

(51) Int. Cl.
*A61B 17/08* (2006.01)
(52) U.S. Cl.
USPC ......................................... 606/153; 606/214
(58) Field of Classification Search
USPC .................. 606/153, 205–209, 214
See application file for complete search history.

(56) References Cited

U.S. PATENT DOCUMENTS

| 5,188,638 | A | * | 2/1993 | Tzakis | 606/153 |
| 6,398,797 | B2 | * | 6/2002 | Bombard et al. | 606/153 |
| 2003/0171775 | A1 | * | 9/2003 | Belson | 606/213 |
| 2003/0236518 | A1 | * | 12/2003 | Marchitto et al. | 606/27 |
| 2005/0192654 | A1 | * | 9/2005 | Chanduszko et al. | 607/116 |
| 2006/0009802 | A1 | * | 1/2006 | Modesitt | 606/215 |
| 2006/0030869 | A1 | | 2/2006 | Loshakove et al. | |
| 2006/0085031 | A1 | | 4/2006 | Bettuchi | |
| 2008/0319461 | A1 | | 12/2008 | Blondeel | |

FOREIGN PATENT DOCUMENTS

| WO | WO 03/061487 A1 | 7/2003 |
| WO | WO 2005/074817 A1 | 8/2005 |
| WO | WO 2007/030892 A1 | 3/2007 |

* cited by examiner

*Primary Examiner* — Corrine M McDermott
*Assistant Examiner* — Alexander Orkin
(74) *Attorney, Agent, or Firm* — Dickstein Shapiro LLP

(57) ABSTRACT

A device for producing anastomoses between a first hollow organ and a second hollow organ including a sheath and an adhesive applicator that can be positioned next to the sheath in order to apply an adhesive to the adhesive bonding section. A method for producing anastomoses between a first hollow organ and a second hollow organ includes folding the first hollow organ over a sheath, positioning the second hollow organ over the first hollow organ, producing a first connection between the hollow organs by applying a high frequency (RF) voltage, and producing a second connection between the hollow organs by applying a tissue adhesive.

23 Claims, 5 Drawing Sheets

DEVICES AND METHODS FOR PRODUCING ANASTOMOSES

CROSS REFERENCE TO RELATED APPLICATIONS

This application claims priority to PCT/EP 2010/004259, filed Jul. 13, 2010 and published as WO 2011/006639, which claims priority to DE102009032972.2, filed Jul. 14, 2009.

FIELD OF THE INVENTION

The disclosed embodiments relate to surgical instruments, and more particularly to surgical instruments used to form anastomoses.

BACKGROUND OF THE INVENTION

An anastomosis is a connection between two anatomical structures. For example, in the course of an organ transplantation, severed blood vessels can be connected with each other by means of anastomoses.

Various methods for producing such anastomoses in surgery are known. The connection can be produced with the use of suturing techniques. Furthermore, there are approaches that allow the organic connection with the use of adhesion techniques. In one example, fibrin sealants are used, thus making possible the highly advantageous connection of organs, in particular hollow organs. However, the tolerability of these sealants or glues is problematic because they may exhibit thrombogenic and toxic properties.

Clamping techniques have also been used to provide a connection at a suitable site. Various aids such as rings, cuffs or stents have been used to aid in producing anastomoses. The disadvantage of these clamping techniques is that they generally remain in the hollow organ to be connected and can trigger rejection reactions and there is also danger of the formation of a thrombus.

From publication WO 03/061487 A1 it is known to connect hollow organs with the application of a suitable high-frequency current (RF current). When the RF current is being applied the tissue structures are being welded together. The cell substance coagulates causing the protein structures to be welded together, so that a controlled, safe, and fast connection can be produced. For the application of the RF current, publication WO 03/061487 A1 describes an instrument comprising an interior sheath and an exterior sheath. Each of these sheaths comprises an electrode which is annular in shape and to which a suitable RF voltage can be applied. Consequently, this is a bipolar electrosurgical instrument. For connecting the ends or end sections of a blood vessel, the first end is passed through the interior sheath and folded over in such a manner that the tissue comes to be placed on the outside of the interior sheath. The second end of the vessel is pulled over the interior sheath and pulled onto the end section of the blood vessel located thereon. The exterior sheath can be opened and slipped over the interior sheath and the tissue located thereon. Consequently, the exterior sheath forms a type of cuff that encloses the individual end sections of the blood vessel. Both the interior sheath and the exterior sheath have an electrode for the application of the RF current. These electrodes are located opposite each other. When the RF current is being applied it flows through the tissue, i.e., the superimposed end sections, thus welding the vessel in place. One problem of the technique described in WO 03/061487 A1 is that the produced connections are frequently not sufficiently stable.

BRIEF SUMMARY OF THE INVENTION

The disclosed embodiments relate to a device for producing anastomoses as well as to a method for producing anastomoses. It is the object of the disclosed embodiments to provide a device for producing an anastomosis between a first and a second hollow organ, that is simple to operate and is suitable for producing high-quality anastomoses.

In one embodiment the anastomoses device produces one or more anastomoses between a first hollow organ and a second hollow organ, where each of the hollow organs has an outer surface and an inner surface. In another embodiment, the anastomoses device includes a sheath, over which the first hollow organ can be folded in such a manner that at least one adhesive bonding section of the inner surface of the first hollow organ comes to be located on the outside and on which the second hollow organ can be positioned over the first hollow organ.

The device may also include an adhesive applicator that can be positioned next to the sheath in order to apply an adhesive to the adhesive bonding section. The adhesive applicator may also facilitate the application of the adhesive. In one disclosed embodiment of the anastomoses device, the sheath acts as the holding device to initially fixate and/or position at least the first hollow organ, for example a blood vessel, in such a manner that the adhesive can be applied. At least a part of the adhesive applicator is positioned next to the sheath for the application of the adhesive. This part may be a nozzle or an outlet that can preferably be arranged opposite the bonding section or the adhesive bonding section so that a preferably direct application of the adhesive thereto can be accomplished. In one embodiment, the adhesive is applied to a section of the folded over inner surface of the first follow organ, namely the bonding section. During a subsequent step, this bonding section may be glued to a section of the inner surface of the second hollow organ.

In accordance with one disclosed embodiment, the anastomoses device can be used for first applying adhesive to the first hollow organ, and then the second hollow organ can be pulled over the first hollow organ. In another embodiment, the first and the second hollow organs can first be positioned, and then the adhesive can be applied to the bonding section. It is a particular feature of the disclosed embodiments that the anastomoses device allows for local, exactly positioned, application of the adhesive.

The anastomoses device may comprise a guide, in which the adhesive applicator or parts of the adhesive applicator are arranged so as to be movable between an accommodation position for accommodating at least the first hollow organ through the sheath and an application position for applying the adhesive. For inserting the first hollow organ into the sheath and for the fold-over procedure it is necessary that sufficient space be available. Therefore, it is advantageous if interfering parts of the adhesive applicator are arranged so that they can be moved back and forth in order to space them sufficiently apart from the sheath when the hollow organ is being accommodated.

In the application position, the first hollow organ can be held in place between the adhesive applicator and the sheath. Consequently, in one embodiment, it is advantageous for the guide of the adhesive applicator to be configured such that at least part of the adhesive applicator may act to fix the first hollow organ in place between the adhesive applicator and the sheath so that the hollow organ cannot slide out of the device.

For introducing the adhesive between the first and the second hollow organs, the adhesive applicator may include at least one adhesive channel. The adhesive channel may be an adhesive capillary. In one embodiment at least one end section of the adhesive channel is arranged or can be arranged essentially parallel to the sheath. Thus, after positioning the first and the second hollow organs in an overlapping region, the adhesive may be introduced between these organs. In one embodiment, this is an overlapping of the inner surfaces of the two hollow organs.

In another embodiment, the anastomoses device may have at least two adhesive channels that are at a defined distance from each other and can be alternately positioned on the sheath. It is advantageous if several adhesive channels are available for the application of adhesive on different sides of the sheath. In one embodiment, there are two adhesive channels that can be alternately positioned on the sheath. The guide may be designed appropriately for such positioning.

The at least one adhesive channel may have a flattened end for the application of the adhesive. This means that the end section of the adhesive channel that is to be used for the application of the adhesive to the tissue, is to act in particular on the inner surface of the first hollow organ so that the second hollow organ can be slipped over without problems. In one embodiment, the device for producing anastomoses makes it possible to first receive the first hollow organ, then provide the adhesive applicator at the appropriate site, and, thereafter, position the second hollow organ. Consequently, no great effort is required for inserting the adhesive applicator between the hollow organs. In one embodiment, the position of the adhesive applicator can be monitored visually.

The adhesive channel may include at least one abutment for positioning the second hollow organ or a section thereof in the longitudinal direction of the sheath. The longitudinal direction of the sheath is defined by the two orifices that connect the sheath channel with each other and that receive the first hollow organ. After positioning the first hollow organ, positioning of the second hollow organ may pose problems. Therefore, in one embodiment, the adhesive applicator features an abutment that, when the second hollow organ is being slipped over the sheath and over the first hollow organ, prevents any poor positioning such as the open ends of the hollow organs not being parallel to each other.

The adhesive channel may include an elbow section having, in particular, an inside angle less than or equal to 90 degrees as the abutment for the second hollow organ. In one embodiment, the at least one adhesive channel has a deformation where the second hollow organ can be positioned.

The sheath can be held on an actuating device and be designed in such a manner that it can be disassembled into at least two parts such that the parts can be moved from a closed state for the formation of an essentially closed pipe section into an open state for removing the connected hollow organ. When the first hollow organ is being accommodated it can be advantageous if the sheath can be disassembled. In one embodiment, after connecting the two hollow organs to form one hollow organ, it must be possible to either disassemble or disconnect the sheath in order to remove the device from the hollow organ.

The anastomoses device may comprise a compression ring that is arranged so as to enclose the sheath, at least in sections, or be arranged in order to fixate the hollow organs, in compression position, in place between the compression ring and the sheath. The compression ring also has the advantage that it holds the hollow organs in place on the sheath. In one embodiment, the compression ring can be arranged and designed in such a manner that it holds the hollow organs in intimate contact with each other such that no adhesive may penetrate through a compression gap between the hollow organs. Therefore, an accommodation region for the adhesive can be created, said region being sealed relative to the interior region of the hollow organs.

In one embodiment, the anastomoses device is an electrosurgical device that comprises electrodes. The sheath may comprise an interior electrode, and the compression ring may comprise an exterior electrode for the application of an RF current. In another embodiment, the anastomoses device may be used to produce a first connection as a result of the applied RF current and a second connection as a result of the adhesive. It has been found that bipolar anastomoses of vessels in adaptation to Payr's Cuff technique display only limited tensile strength. In order to eliminate this disadvantage, the disclosed embodiments provide that an additional adhesive connection be provided, the connection connecting additional sections, in particular in the region of the end sections of the hollow organs, and thus increasing the strength of the overall connection. In one embodiment, the RF current can be applied by means of the compression ring. Following the application of the RF current and the resultant first continuous connection of the organs, the adhesive may be introduced. The produced welding connection may act as a delimiting feature so that the adhesive will not spread further into the organ that is to be connected.

The adhesive applicator may be detachably connected to the device, thus making device handling easier. In one embodiment, known RF instruments are upgraded with the adhesive applicator in accordance with the disclosed embodiments. Furthermore, it is possible to attach the potentially interfering adhesive applicator to the device only when said applicator is required. For example, in one embodiment, attaching the adhesive applicator may only be advantageous when a welding connection has already formed between the organs with the use of RF current.

The adhesive applicator may include a feed line of non-adhesive material. For example, the non-adhesive material may be polytetrafluoroethylene (PTFE). An appropriate selection of material can prevent the adhesive from clogging the feed line.

The adhesive applicator may include an adhesive reservoir and a compressor for the application of the adhesive. The compressor is used to provide a propellant by means of which the adhesive is driven through the feed line so that the adhesive can be applied at a suitable site of the hollow organs. The compressor may be a syringe.

The disclosed embodiments also include a method for producing anastomoses between a first hollow organ and a second hollow organ, where each of the hollow organs has an inner surface. The method in accordance with the disclosed embodiments may include a folding over of the first hollow organ over a sheath, so that at least one adhesive bonding section of the inside surface of the first hollow organ comes to be on the outside. Furthermore, the method may include a positioning of the second hollow organ over the first hollow organ and a formation of a first connection with the hollow organs. The first connection may include applying an RF voltage. A second connection may be produced between the hollow organs by applying a tissue adhesive.

In one embodiment, the tissue adhesive is introduced between the superimposed hollow organs. The tissue bonding section may be covered, at least in sections, with the tissue adhesive. The method, in accordance with the disclosed embodiments, may result in the formation of two connections between the hollow organs. In one embodiment, the first connection is due to electrosurgical coagulation, whereas the second connection is produced by chemical means. Due to this dual connection, the produced anastomosis can be subjected to substantially more strain, in particular to more tensile forces than were previously attainable.

The first connection can include the application of the RF voltage to the sheath, in particular an interior electrode of the sheath, and an exterior electrode. In one embodiment, the exterior electrode contacts at least one of the hollow organs so that an applied RF current passes through the hollow organs, thus connecting them to each other.

The method can include an application of a compression ring and an application of a predefined force by means of the compression ring. The compression ring can be used to fixate the hollow organs in place on the sheath so that the organs are held in the prespecified position. Furthermore, the compression ring can be used for applying a predefined force that aids the formation of the first connection. The compression ring may also ensure that, while the second connection is being produced, the tissue adhesive does not enter the inside/lumen of the hollow organ(s).

In one embodiment, the second connection can be produced by injecting the tissue adhesive into an intermediate space between the hollow organs. While the tissue adhesive is being injected, the compression ring may be particularly helpful because it holds the hollow organs together in a fluid-tight manner relative to the outside region.

In one example, the second connection may be produced after the first connection has been produced. To this extent, the aforementioned effect can be utilized in a particularly positive manner. The first connection can be produced in such a manner that an adhesive region remains between the first and the second hollow organs for the accommodation of the tissue adhesive, in which case the adhesive region is sealed in a fluid-tight manner relative to the inside region of the hollow organs.

The adhesive region may be a region between the hollow organs, said region being located distally to the first connection (i.e., on the side on which the hollow organs are open). This adhesive region may include the already mentioned adhesive bonding section, for example. The connection produced with the use of RF coagulation may seal the hollow organs in such a manner that the adhesive cannot penetrate into the lumen. Preventing penetration into the lumen, may be ensured even if the adhesive is injected into the adhesive region at a relatively high pressure.

DETAILED DESCRIPTION OF THE INVENTION

In the description hereinafter, the same reference signs are used for the same parts and for parts having the same function.

Figure 1:
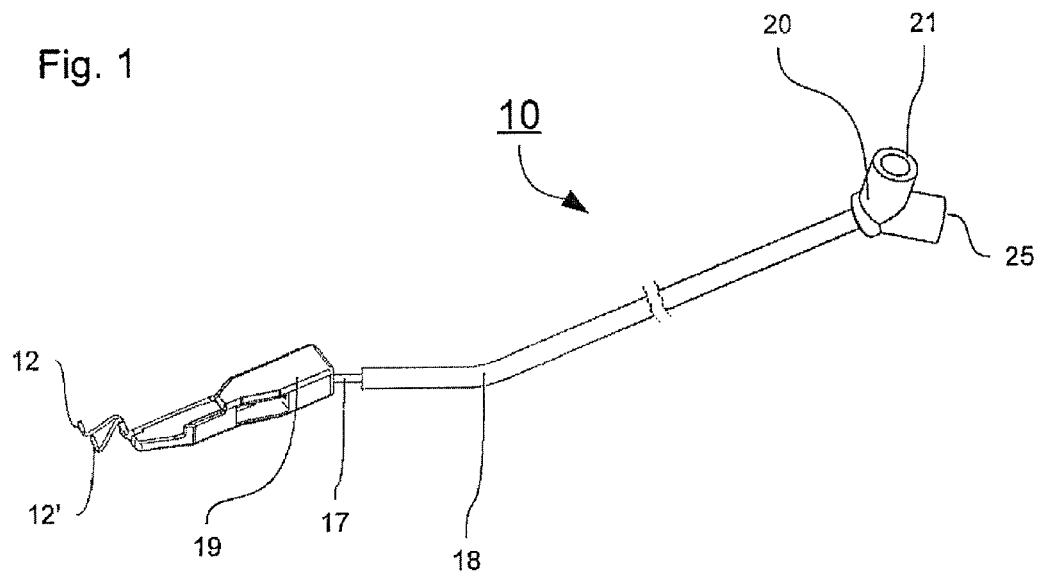
FIG. 1 is an adhesive applicator in accordance with a disclosed embodiment.

FIG. 1 shows an adhesive applicator 10 that can be detachably connected to a device for producing anastomoses, e.g., an electrosurgical instrument 1 (FIGS. 4 through 8).

The adhesive applicator 10 includes an adapter 19 with adhesive capillaries 12, 12', a feed pipe 18, and a coupling piece 20. The coupling piece 20 represents the proximal end of the adhesive applicator 10, whereby the coupling piece 20 is connected with the adhesive capillaries 12, 12' via the feed pipe 18 and a feed line 17. The coupling piece 20 may be Y-shaped and includes an adhesive connecting orifice 21 and a propellant connecting orifice 25. Via the adhesive connecting orifice 21, an adhesive can be introduced into the feed pipe 28. A propellant may be pumped into the feed pipe 18 via the propellant connecting orifice 25 in a time-delayed manner driving the adhesive through the feed pipe 18 in the direction toward the distal end of the adhesive applicator 10. In one embodiment, the adhesive capillaries 12, 12' and/or the feed line 17 consist of stainless steel, and the feed pipe 18 is made of non-adhesive material such as, for example, PTFE. In one embodiment, the feed pipe 18 is flexible and has a length of not more than 50 cm. Preferably, the feed pipe 18 has a length of 10 cm to 30 cm. Any adhesion inside the adhesive applicator 10 is prevented due to the configuration, the selection of material, and the length of the feed pipe 18, the feed line 17 and the adhesive capillaries 12, 12'.

An adhesive reservoir (not shown) that is connected to the adhesive connecting orifice 21 may be a tube containing the adhesive. A compressor or a corresponding compressor system connected to the propellant connecting orifice 25 may be a commercially available medical syringe, for example.

Figure 2:
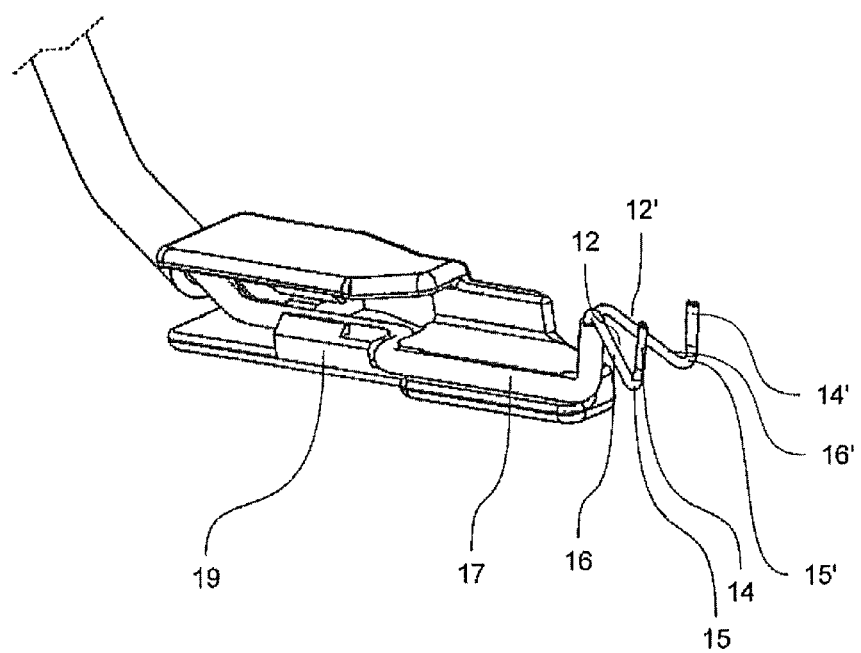
FIG. 2 is a side view of the distal end of an adhesive applicator in accordance with FIG. 1.
Figure 3:
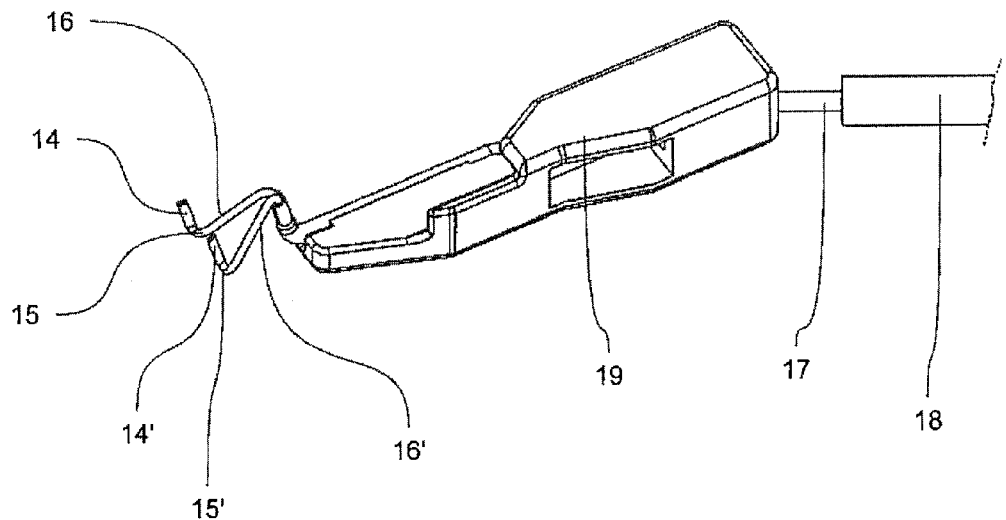
FIG. 3 is a side view of the distal end of an adhesive applicator in accordance with FIG. 1.

As shown in FIGS. 2 and 3, the feed pipe 18 terminates distally in the feed line 17 that is passed through the adapter 19. The feed line 17 terminates on the distal end in the first adhesive capillary 12 and the second adhesive capillary 12'. Consequently, the feed line 17 branches into the two adhesive capillaries 12, 12'. The last section of the feed line 17 extends essentially perpendicularly with respect to the longitudinal direction of the adapter 19. Directly downstream of the division into the two adhesive capillaries 12, 12', there may be adjoining a downward inclined first connecting section 16 having a first elbow section 15 and a first vertical section 14 or a downward inclined second connecting section 16' having a second elbow section 15' and a second vertical section 14'. The vertical sections 14, 14' extend essentially parallel to the vertically extending end section of the feed line 17. Hence, the orifices of the adhesive capillaries 12, 12' point upward.

Figure 4:
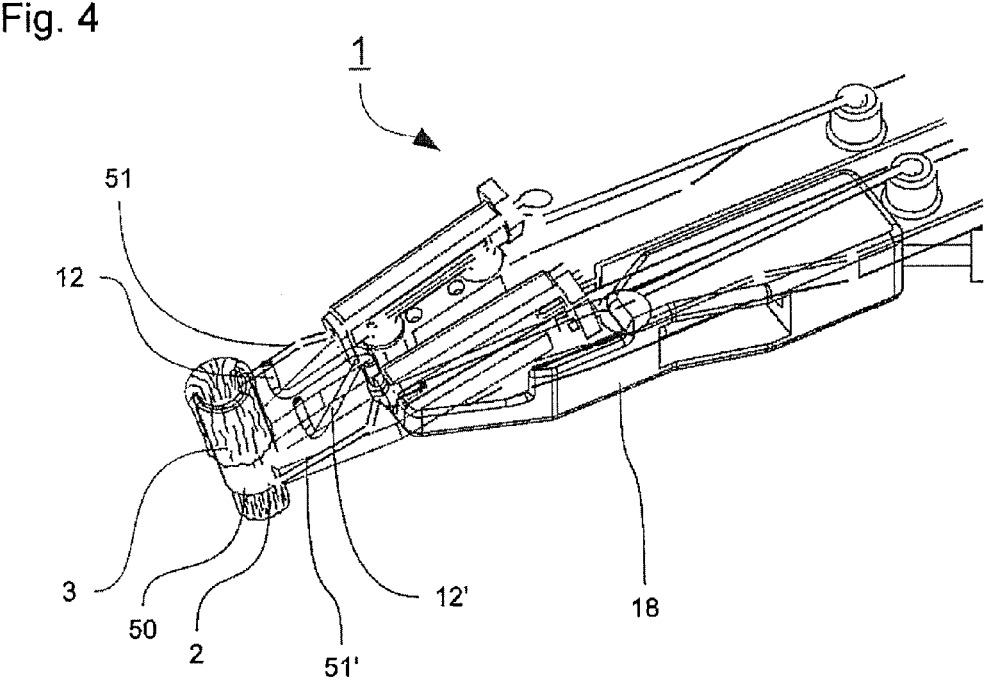
FIG. 4 is an electrosurgical instrument for producing anastomoses with an adhesive applicator in accordance with FIG. 1, showing the adhesive applicator being positioned on the instrument.
Figure 5:
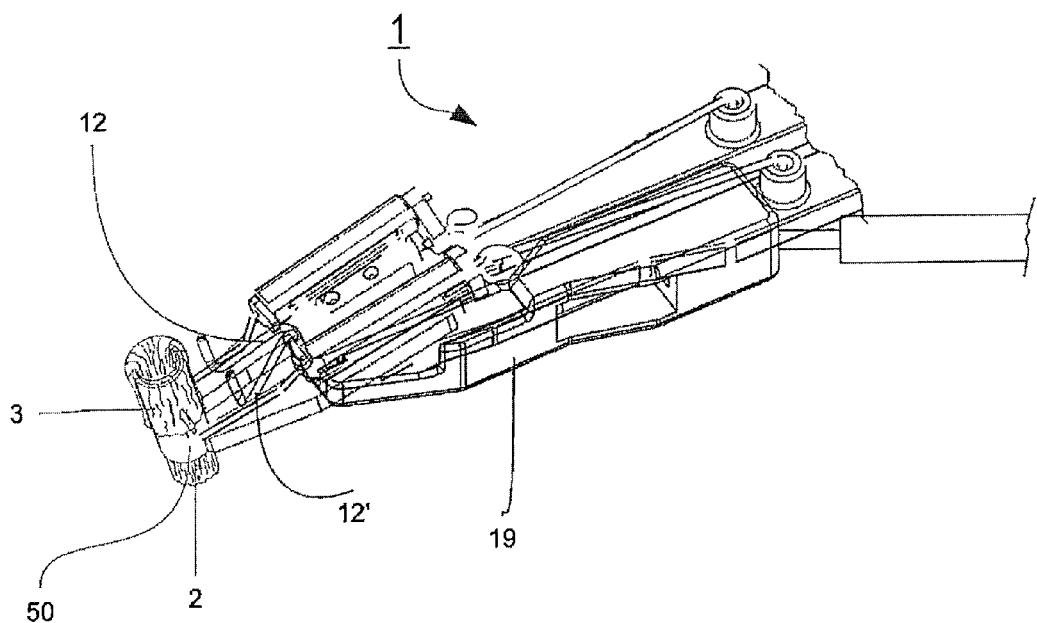
FIG. 5 is an electrosurgical instrument for producing anastomoses with an adhesive applicator in accordance with FIG. 1, showing the adhesive applicator being positioned on the instrument.

The adhesive applicator 10 may be a part of the electrosurgical instrument 1 and can be connected with said instrument. FIGS. 4 and 5 show the electrosurgical instrument 1 while the adhesive applicator 10 is being positioned. The electrosurgical instrument 1 includes a sheath 50 for the accommodation of a first vessel section 2, as well as two sheath actuating devices 51, 51' by means of which the sheath 50 (that is divided into two parts) can be brought into an opened and a closed position. In the closed position, the sheath 50 forms a pipe in which the first vessel section 2 (e.g., a blood vessel) can be placed. After the first vessel section 2 has been inserted through the sheath 50, the vessel can be folded over in such a manner that the folded over end encloses the sheath 50. FIG. 4 shows a folded over tissue section 3 of the first tissue section 2. The inner surface of the folded over tissue section 3 faces outward. In the position shown in FIG. 4, the adhesive applicator 10 is shown in a receiving position, in which the vertical sections 14, 14' are at a distance from the sheath 50. The folding over procedure can be performed without any interference of the adhesive applicator 10.

FIG. 5 also shows the folded over tissue section 3 that is positioned on the sheath 50.

Figure 6:
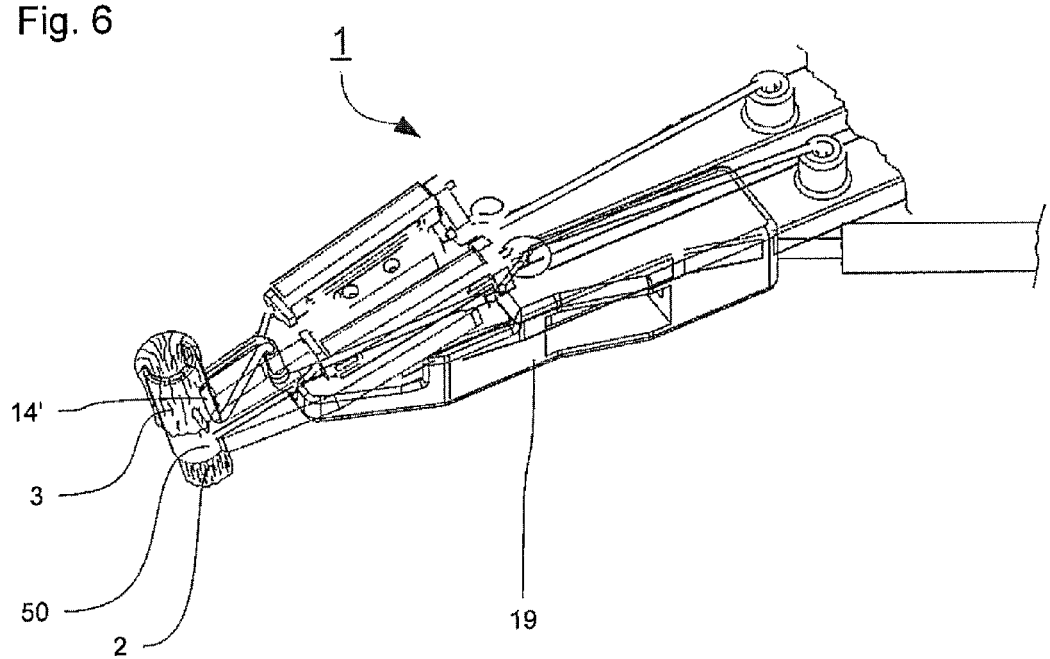
FIG. 6 is an electrosurgical instrument in accordance with FIG. 5, showing the adhesive applicator in position.

FIG. 6 shows the adhesive applicator 10 in an application position in which the vertical sections 14, 14' are located on the folded over tissue section 3 and fixate said tissue section 3 in place between the vertical sections 14, 14' and the sheath 50. The vertical sections 14, 14' are alternately positioned relative to the sheath 50 and extend essentially parallel to the sheath channel of the sheath 50. The orifices of the nozzles of the adhesive capillaries 12, 12' point upward.

Figure 7:
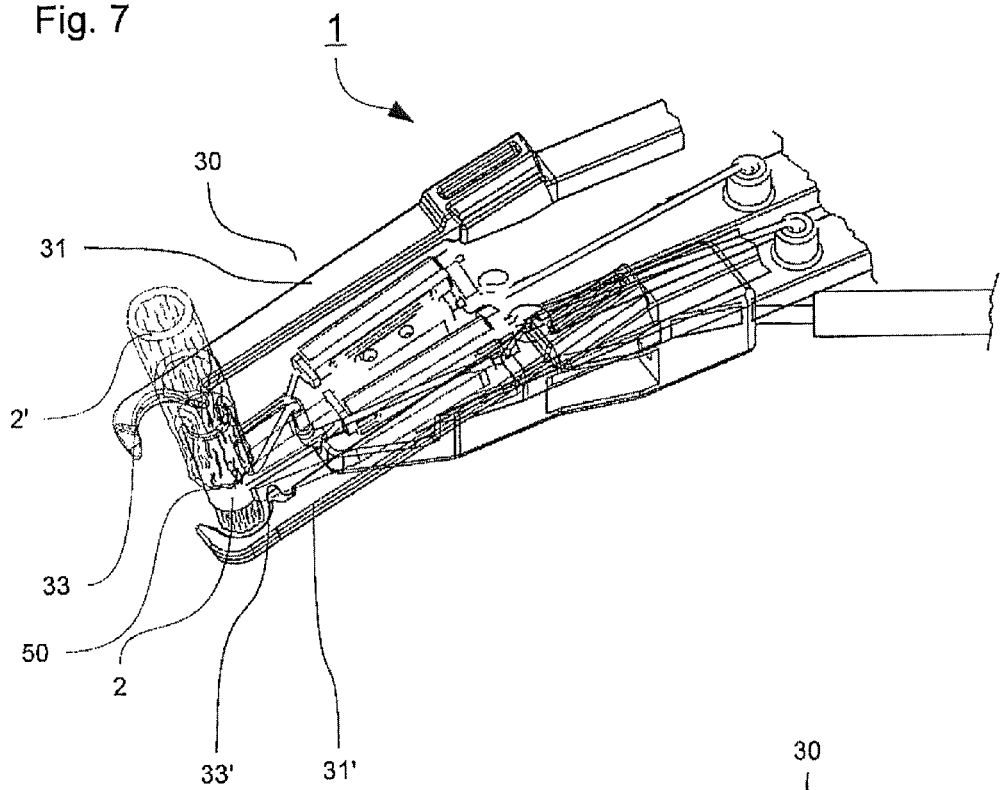
FIG. 7 is an electrosurgical instrument in accordance with FIG. 6, showing the compression forceps opened.
Figure 8:
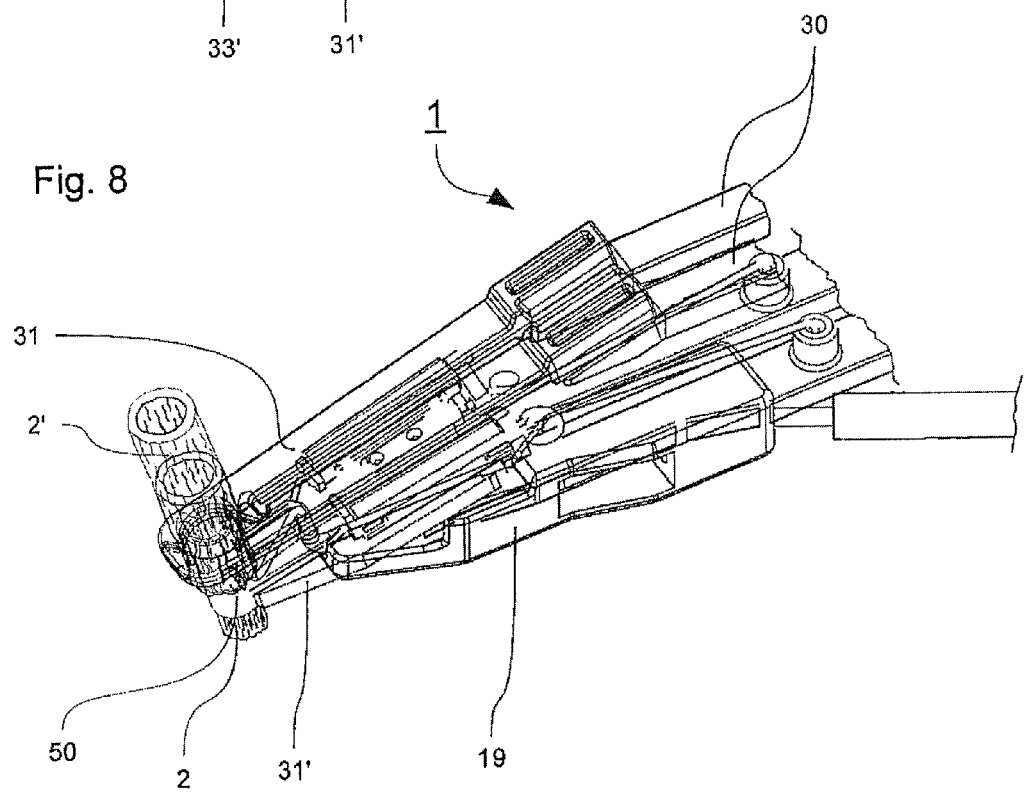
FIG. 8 is an electrosurgical instrument in accordance with FIG. 6, showing the compression forceps closed.

In FIG. 7, a second vessel section 2' that is to be connected to the first vessel section 2 is pulled over the folded over tissue section 3. Furthermore, a compression forceps 30 is attached to the adapter 19 at this point. The compression forceps 30 has a first branch 31 and a second branch 31' that are alternately attached relative to the sheath 50. FIG. 8 shows the branches 31, 31' in attached state, in which case said branches are in a compression position, thus fixating the vessel sections 2, 2' in place on the sheath 50 so as to be resiliently pretensioned.

When positioning the second vessel section 2', the adhesive capillaries 12, 12' are placed tightly enough on the folded over tissue section 3 so that the second vessel section 2' is slipped over said adhesive capillaries 12, 12'. The elbow sections 15, 15' act as limiting features. They simplify any positioning of the second vessel section 2' along a longitudinal direction 56 of the sleeve 50. The second vessel section 2' may be slipped over the sheath 50 until the open end abuts against the elbow sections 15, 15'.

Figure 9:
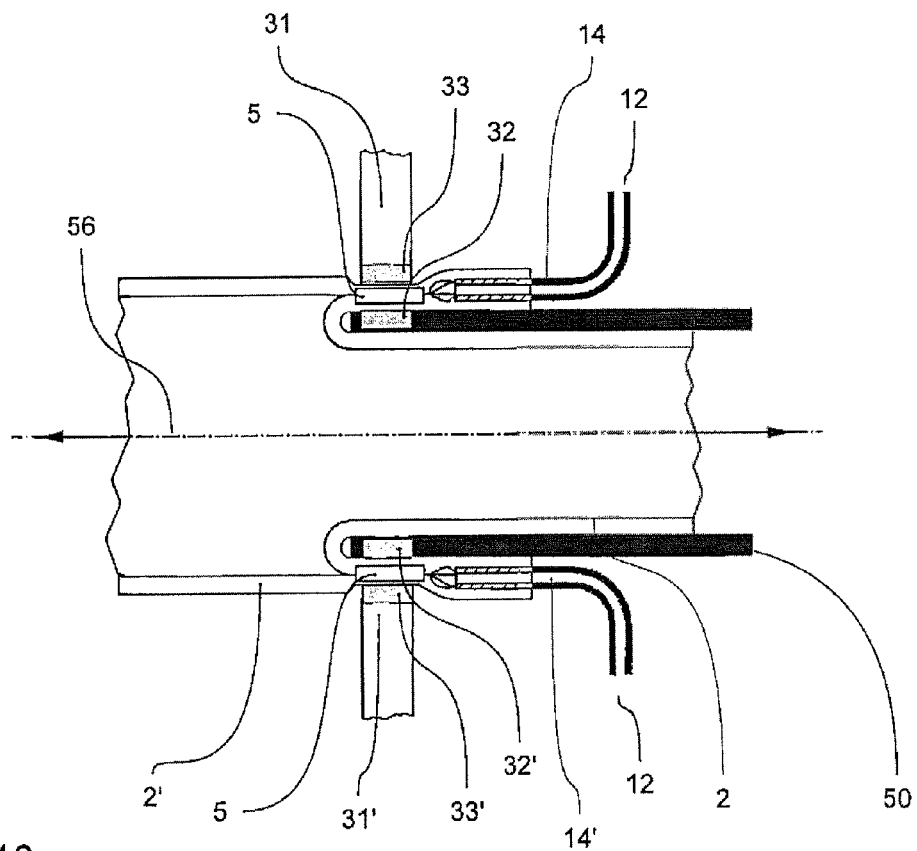
FIG. 9 is a schematic representation of the longitudinal section of a device for producing anastomoses in accordance with a disclosed embodiment.

FIG. 9 shows a schematic longitudinal cross-section along the longitudinal direction 56 of the sheath 50 through the vessel sections 2, 2' and the electrosurgical instrument 1, i.e., through the sheath 50, the compression forceps 30, and the adhesive capillaries 12, 12'. The vessel sections 2, 2' are placed in the electrosurgical instrument 1, and the compression forceps 30 is in compression position. A substantial section of the first vessel section 2 extends inside the sheath 50. The folded over tissue section 3 is situated folded over on the outside surface of the sheath 50, whereby the inner surface of tissue section 3 faces outward. Situated on this section of the inner surface of the first vessel section 3 is a section of the inner surface of the second vessel section 2'. Overall, the vessel sections 2, 2' extend along the longitudinal axis 56. Close to the upper end of the sheath 50, the sheath 50 is enclosed by the compression forceps 30. The branches 31, 31' fixate the sections of the first and the second vessel sections 2, 2' in place on the sheath 50. On the side facing the sheath 50, the first branch 31 includes a first exterior electrode 33, and the second branch 31 includes a second exterior electrode 33'. The sheath 50 comprises an annular interior electrode 32 that extends along the outside surface. The exterior electrodes 33, 33' are arranged opposite the interior electrode 32. They contact the overlapping vessel sections 2, 2' and can be connected to an RF generator so that an RF voltage can be applied to said vessel sections. An applied RF current flows through the vessel sections 2, 2' and results in a fusion of the tissue. An annular tissue connection 5 is formed, said connection connecting the vessel sections 2, 2'.

FIG. 9 shows the vessel sections 2, 2' with the annular tissue connection 5. The adhesive capillaries 12, 12' are inserted on the open end of the overlapping vessel sections 2, 2' beyond the tissue connection 5. By way of the capillaries, it is possible to introduce the adhesive that connects the vessel sections 2, 2'.

Figure 10:
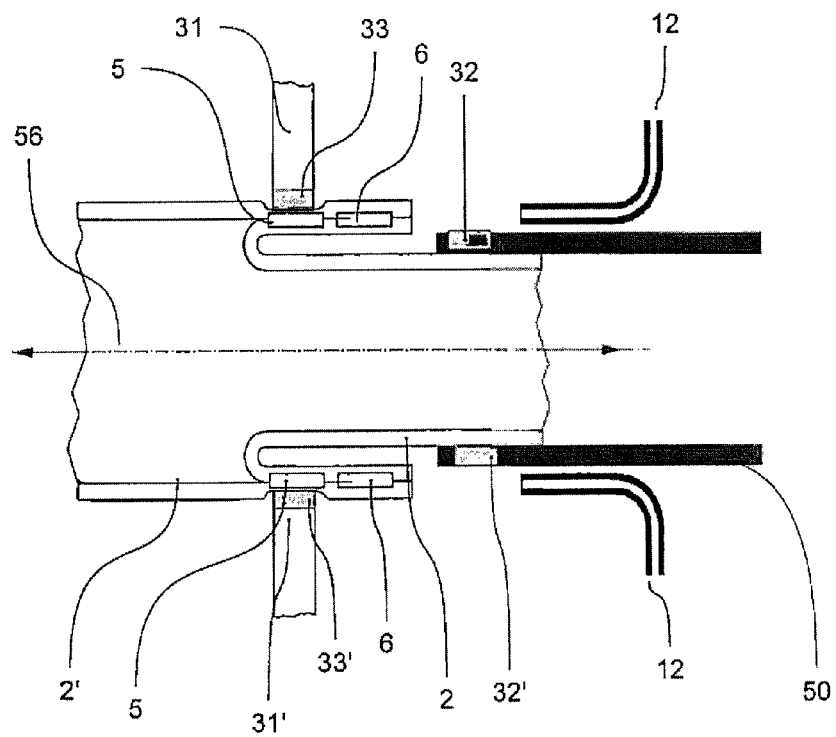
FIG. 10 is a schematic representation in accordance with FIG. 9, showing the instrument being removed.

FIG. 10 shows the adhesive connection 6 between the vessel sections 2, 2'. Preferably, the adhesive is introduced between the vessel sections 2, 2' in such a manner that the adhesive connection 6 also extends in an annular manner along the tissue connection 5. Following the application of the adhesive, the electrosurgical instrument 10 comprising the sheath 50 and the adhesive capillaries 12, 12' can be removed. The tissue connection 5 that is produced chronologically prior to the adhesive connection 6 prevents the penetration of the adhesive into the inside of the connected vessels. The adhesive connection 6 strengthens the bond between the vessel sections 2, 2'. Because of the adhesive connection 6, the vessel sections 2, 2' can also absorb higher stress in the longitudinal direction.

Although the disclosed embodiments has been described here in conjunction with an electrosurgical instrument 1, the disclosed embodiments can also be used without the electrosurgical instrument 1.

Although an adhesive applicator is described including only two adhesive capillaries 12, 12'. It should be understood that several adhesive capillaries 12, 12' on the electrosurgical instrument 1 or on any other medical device may be included. In another embodiment, the device for producing anastamoses includes a guide by which the capillaries 12, 12' can be rotated about the sheath 50 in order to produce a continuous adhesive connection 6. In a method in accordance with the disclosed embodiments an adhesive connection 6 is to be produced, the connection may extend ring-like around the sheath 50. However, in another embodiment the adhesive connection 6 may only be applied in sections.

The invention claimed is:

1. A device for producing anastomoses between a first hollow organ and a second hollow organ, wherein each of the hollow organs comprises an outer surface and an inner surface, the device comprising:

a sheath, configured such that the first hollow organ can pass through a center of the sheath and be folded over such that at least one section of the inner surface of the first hollow organ comes to be located adjacent an outside surface of the sheath, the sheath further being configured such that the second hollow organ can be positioned over the first hollow organ such that at least one section of the inside surface of the second hollow organ is in contact with the at least one section of the inside surface of the first hollow organ; and an adhesive applicator configured to apply adhesive between and in contact with both the inside surfaces of the first and second hollow organs, wherein the adhesive applicator comprises at least one adhesive channel with at least one section, the at least one section of the adhesive channel arranged parallel to the sheath for introducing an adhesive between the first and the second hollow organs, wherein the at least one adhesive channel has at least one guide for positioning the second hollow organ in a longitudinal direction of the sheath, and wherein the at least one guide is integrated into the adhesive channel such that the adhesive channel comprises an elbow section having an inside angle smaller than or equal to 90° as an abutment guide for positioning the second hollow organ.

2. The device for producing anastomoses as in claim 1, wherein the adhesive applicator has an application position for the application of an adhesive and an accommodation position, wherein in the accommodation position, the sheath and the adhesive applicator are configured to allow the first hollow organ through the sheath.

3. The device for producing anastomoses as in claim 2, further comprising at least one set-point that fixes at least one of the application position and accommodation position of the adhesive applicator.

4. The device for producing anastomoses as in claim 2, wherein the device is configured such that when the adhesive applicator is in the application position, the first hollow organ can be fixated between the adhesive applicator and the sheath.

5. The device for producing anastomoses as in claim 1, further comprising at least two adhesive channels positioned at a fixed distance from each other.

6. The device for producing anastomoses as in claim 5, wherein the at least two adhesive channels are positioned on either side of the sheath.

7. The device for producing anastomoses as in claim 1, wherein the adhesive channel has a flattened end for the application of the adhesive.

8. The device for producing anastomoses as in claim 1, wherein the sheath is connected to an actuating device, wherein the sheath and the actuating device are configured such that the sheath and the actuating device can be disassembled into at least two parts such that the parts can be moved from a closed state for forming an essentially closed pipe section to an open state for removing the first and second hollow organs.

9. The device for producing anastomoses as in claim 1, further comprising a compression ring configured to enclose at least a section of the sheath.

10. The device for producing anastomoses as in claim 9, wherein the compression ring is configured to fixate the hollow organs in a compression position in place between the compression ring and the sheath.

11. The device for producing anastomoses as in claim 9, wherein the sheath further comprises an interior electrode and the compression ring comprises an exterior electrode for the application of an RF current.

12. The device for producing anastomoses as in claim 1, wherein the adhesive applicator is detachably connected to the device.

13. The device for producing anastomoses as in claim 1, wherein the adhesive applicator comprises a feed line.

14. The device for producing anastomoses as in claim 13, wherein the feed line is formed of a non-adhesive material.

15. The device for producing anastomoses as in claim 13, wherein the feed line material comprises polytetrafluoroethylene (PTFE).

16. The device for producing anastomoses as in claim 13, wherein the adhesive applicator further comprises an adhesive reservoir and a compressor for the application of the adhesive.

17. The device for producing anastomoses as in claim 16, wherein the compressor is a syringe.

18. The device for producing anastomoses as in claim 16, wherein the adhesive applicator further comprises a coupling for connection of the adhesive reservoir and the compressor.

19. A method for producing anastomoses between a first hollow organ and a second hollow organ by means of an anastomoses device, wherein each of the hollow organs has an inner surface, the method comprising:
   folding the first hollow organ over a sheath such that at least one adhesive bonding section of the inner surface of the first hollow organ comes to be located outside;
   positioning the second hollow organ over the first hollow organ and using at least one guide comprising an elbow section with an inside angle smaller than or equal to 90° as an abutment guide for positioning the second hollow organ;
   producing a first connection between a section of the inner surfaces of the hollow organs by applying an RF voltage; and
   producing a second connection between the section of the inner surfaces of the hollow organs by applying a tissue adhesive via an adhesive applicator integrated into the at least one guide.

20. The method for producing anastomoses as in claim 19, wherein producing the first connection comprises applying the RF voltage through the sheath comprising an interior electrode, and through an exterior electrode contacting at least one of the hollow organs.

21. The method for producing anastomoses as in claim 19, further comprising:
   providing a compression ring to fixate the hollow organs in place between the compression ring and the sheath; and
   applying a predefined force with the compression ring to aid formation of the first connection.

22. The method for producing anastomoses as in claim 19, wherein the second connection is formed after the first connection has been formed.

23. The method for producing anastomoses as in claim 19, wherein the first connection is formed such that an adhesive region remains between the first and the second hollow organs for the accommodation of the tissue adhesive, and wherein the first connection is formed such that the adhesive region is sealed in a fluid-tight manner relative to an inside region of the hollow organs.

* * * * *